United States Patent [19]
Samuelsen

[11] Patent Number: 6,051,249
[45] Date of Patent: *Apr. 18, 2000

[54] DRESSING HAVING A THREE-DIMENSIONAL PART AND PROCESSES FOR THE PREPARATION OF SUCH A DRESSING

[75] Inventor: Peter Boman Samuelsen, Rungsted Kyst, Denmark

[73] Assignee: Coloplast A/S, Humlebaek, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/875,421
[22] PCT Filed: Jan. 26, 1996
[86] PCT No.: PCT/DK96/00043
§ 371 Date: Jul. 28, 1997
§ 102(e) Date: Jul. 28, 1997
[87] PCT Pub. No.: WO96/22754
PCT Pub. Date: Aug. 1, 1996

[30] Foreign Application Priority Data
Jan. 27, 1995 [DK] Denmark .................................. 0096/95

[51] Int. Cl.[7] ...................................................... A61F 13/00
[52] U.S. Cl. ........................ 424/443; 602/61; 602/62; 602/63; 602/901; 604/304; 604/308
[58] Field of Search .............................. 424/443; 602/61, 602/62, 63, 901, 304, 308

[56] References Cited

U.S. PATENT DOCUMENTS

| | | | |
|---|---|---|---|
| 2,243,422 | 5/1941 | Hollander et al. | 128/165 |
| 2,847,005 | 8/1958 | Bourne | 128/157 |
| 2,875,758 | 3/1959 | Fuzak et al. | 128/157 |
| 3,348,541 | 10/1967 | Loebeck | 128/157 |
| 3,476,109 | 11/1969 | Hurney | 604/308 |
| 3,809,096 | 5/1974 | York | 128/403 |
| 3,972,328 | 8/1976 | Chen | 128/156 |
| 4,240,436 | 12/1980 | Singleton | 128/403 |
| 4,367,732 | 1/1983 | Poulsen et al. | 128/156 |
| 4,671,267 | 6/1987 | Stout | 128/156 |
| 4,867,748 | 9/1989 | Samuelsen | 604/336 |
| 4,961,732 | 10/1990 | Stienstra | 604/293 |

FOREIGN PATENT DOCUMENTS

| | | |
|---|---|---|
| 147226 | 5/1984 | Denmark . |
| 0 055 023 | 6/1982 | European Pat. Off. . |
| 0 092 999 | 11/1983 | European Pat. Off. . |
| 0 573 708 | 12/1993 | European Pat. Off. . |
| WO90/03155 | 4/1990 | WIPO . |
| WO92/05756 | 4/1992 | WIPO . |

Primary Examiner—D. Gabrielle Brouillette
Attorney, Agent, or Firm—Jacobson, Price, Holman & Stern, PLLC

[57] ABSTRACT

A dressing comprising a body facing layer of a thermoplastic adhesive and a carrier film and an absorbent material, the dressing having in itself an outwardly facing convex surface and an inwardly facing concave surface, wherein the dressing comprises a first area facing the wound or skin, the area having essentially three-dimensional geometry and optionally a second area, the first area preferably comprising a hydrocolloid adhesive and a carrier film, and the second area essentially showing adhesive properties and preferably comprising a carrier film and a hydrocolloid adhesive and wherein the adhesive in one or both areas is optionally covered by one or more layers to be removed before use.

12 Claims, 1 Drawing Sheet

DRESSING HAVING A THREE-DIMENSIONAL PART AND PROCESSES FOR THE PREPARATION OF SUCH A DRESSING

This application is a 371 of PCT/DK96/00043, filed Jan. 26, 1996.

FIELD OF THE INVENTION

The present invention relates to dressings, in particular dressings for covering a protruding or a retracted part of the body, methods for preparing such dressings, the use of blanks in the form of a combined film for preparing such dressings and a method of treating a wound on a protruding part of the body.

BACKGROUND OF THE INVENTION

Conventionally, dressings for the treatment of wounds or pressure sores are essentially flat dressings which are sufficiently conformable to be applied to flat or curved areas of the body and possess a sufficient absorbent capacity to absorb wound exudate. Such flat dressings are not very suitable for applying on protruding parts of the body such as elbows, heels or the tips of fingers or toes.

Published EP application No. 0 573 708 discloses a process for the forming of means comprising hydrocolloid adhesives for wound treatment. This reference discloses production of means or dressings for treatment of wounds which means or dressings can be prepared in a continuous manner.

Published EP application No. 0 092 999 discloses an occlusive wound dressing which may be used for treatment of wounds on the skin and a particulate or granular material being able to act together with the exudate of the wound. Wounds secreting vast amounts of liquid may be treated by firstly applying the granulate material and then to cover the wound with the material for treating wounds. This reference is silent with respect to three-dimensional dressings and concentrate on wounds or damages from which a considerable amount of liquid is secreted.

U.S. Pat. No. 4,876,748 discloses a dressing containing a water-soluble or water-swellable hydrocolloid, a water-insoluble, viscous elastomeric binder and optionally a tackifier resin which is bevelled along all outer edges and optionally also, if annular, along the inner edge.

U.S. Pat. No. 4,367,732 discloses a skin barrier consisting of an elastic film, secured to the film a layer of at least weakly elastic adhesive material, these two components together having low resistance to quick deformation and rapid recovery to substantially the original shape after deformation, the plastic properties of the adhesive thereby being compensated by the elasticity of the film. Optionally there may be a protective cover on the other side of the adhesive layer. The adhesive material consists of a hydrocolloid dispersed in a continuous phase consisting of a mixture of a physically cross-linked elastomer, a hydrocarbon resin tackifier, a plasticizer for the elastomer, an antioxidant and optionally an oily extender. This reference does not disclose three-dimensional dressings.

DK patent No. 147,226 discloses a dressing having an adhesive layer and a water-proof polymer film. The dressing comprises a layer of pressure-sensitive adhesive and a water-impermeable flexible polymer film in which the adhesive comprises a rubbery elastomer in which is distributed a water-soluble or water-swellable hydrocolloid or a mixture of hydrocolloids, a tackifying resin and a plasticizer. Between the adhesive layer and the flexible polymer film is a layer of flexible foam having semi-open cells. The reference does not disclose three-dimensional dressings.

Published EP application No. 0 055 023 discloses an antiseptic adhesive comprising a natural or synthetic viscous rubbery mixture having one or more water-swellable hydrocolloids and antiseptic agents. It has been shown that having one or more antiseptic agents incorporated in the adhesive, the probability of bacterial growth will be reduced considerably and in many cases be totally avoided. The healing effect does not seem to be adversely afflicted. This reference does not mention three-dimensional dressings.

U.S. Pat. No. 3,348,541 discloses a prepared bandage complementary to the end of a finger including at least the first joint thereof, and having an adhesive strip for holding the bandage on the finger.

U.S. Pat. No. 2,847,005 discloses a surgical dressing for forming a finger cot. The dressing comprises an elongated flexible member permanently formed as an arcuate trough for disposition longitudinally along the outer surface of a finger, said trough including an open rear end and a closed forward end portion, and comprising a part to be folded over the finger once placed in the trough. The part to be folded over the finger comprises a strip of adhesive along its edge adhering to the finger.

U.S. Pat. No. 2,875,785 discloses a finger tip bandage having a central cornpress or protecting pad with adjoining adhesive areas in the form of a flat sheet having two pairs of notches to allow bending the bandage to fit the finger.

U.S. Pat. No. 2,243,422 discloses a finger bandaging unit comprising a gauze pad having substantially rectangular body and a tab portion extending from one edge thereof and adhesive-surfaced securing means carried by said pad.

Published International Patent Application No. WO 92/05756 discloses a conformable wound dressing of concavo-convex or cup-like shape comprising a body facing layer of an apertured elastomeric material having a concave nonadherent wound contacting surface, an outer layer of bacteria impermeable moisture vapor transmitting elastomeric film having an outwardly facing convex surface and an extensible intermediate layer of absorbent material which may be a sheet of polymer foam. The dressing is made from a flat blank.

None of the above references disclose nor indicate the existence of three-dimensional dressings for covering a protruding part of the body, said dressing having a three-dimensional part having an adhesive surface for contacting the wound.

One object of the invention is to provide a dressing, for example a finger tip or toe tip dressing allowing the choice of materials and form of the dressing ensuring an improved healing and a dressing being simple to produce and to apply to the wound to be covered. Another object of the invention is to provide a dressing which may prevent e.g. wearing or abrasion damages, e.g. on heels or elbows, and are provided with a surface which may be adapted to the environment in which the dressing is to be used giving a longer effective time of use for the dressing between the change the dressing. A further object of the invention is to provide a dressing which comprises emollients or e.g. retinoids for treating or preventing formation of psoriasis, eczema, callous skin, corns or blisters. A still further object of the invention is to provide processes for the preparation of such dressings.

BRIEF DESCRIPTION OF THE INVENTION

The invention relates to a dressing comprising a body facing layer of a thermoplastic adhesive and a carrier film, said dressing having an outwardly facing convex surface and having absorbing properties.

Furthermore, the invention relates to a method for producing a dressing comprising a body facing layer of a thermoplastic adhesive by drawing or vacuum forming.

A further aspect the invention relates to a method for producing a dressing comprising a body facing layer of a thermoplastic adhesive by moulding, e.g. by injection moulding.

Still further, the invention relates to the use of a combined film comprising a release layer, a hydrocolloid adhesive and a carrier film for producing a dressing comprising a carrier film and a body facing layer of a thermoplastic adhesive.

The invention also relates to a method of treating a wound on a protruding or retracting part of the body comprising applying a dressing comprising carrier film and a body facing layer of a thermoplastic adhesive, said dressing having an outwardly facing convex or concave surface and having absorbing properties.

BRIEF DESCRIPTION OF THE DRAWINGS

The invention is explained more in detail with reference to the drawings in which.

DETAILED DESCRIPTION OF THE INVENTION

In a first aspect, the invention relates to dressing comprising a carrier film and a body facing layer of a thermoplastic adhesive having absorbing properties, said dressing having in itself an outwardly facing convex surface and an inwardly facing concave surface, wherein said dressing comprises a first area facing the wound or skin, said area having essentially three-dimensional geometry and optionally a second area, said first area preferably comprising a hydrocolloid adhesive and a carrier film, and said second area essentially showing adhesive properties and comprising a carrier film and an adhesive, preferably a hydrocolloid adhesive, and wherein the adhesive in one or both areas is optionally covered in part or fully by one or more layers to be removed before use.

Such dressings comprising a first area facing the wound or skin, said area having essentially three-dimensional geometry and a second area optionally having an essentially two-dimensional geometry, said first area comprising a hydrocolloid adhesive are novel.

The first area of the dressing according to the invention offers the option of individual adaptation to extremities having a great curvature as for example joints, fingers, noses, heels and toes and facilitates the application of the dressing embracing the part of the body to which it is applied. At the same time, the adhesive which may be antiseptic may come into close contact with the skin limiting or avoiding the risk of infection with bacteria. Furthermore, an easy application is obtained, especially for finger dressings which may be applied using only one hand, e.g. by the user himself without help from an assisting person. By forming the first areas of the dressing embracing the wound as essentially three-dimensional, curved areas, joints adjacent to the wound are avoided increasing the security against leaks and bacterial infection. These advantages are supported by using a hydrocolloid adhesive ensuring a firm grip when used with bleeding wounds or wounds secreting an exudate as the liquid is absorbed by the hydrocolloid and thus will not disturb the adhesion of the dressing to the skin. Using a hydrocolloid adhesive also enables longer periods of use of the dressing between changing the dressing due to the skin-compatibility of such adhesive.

Figure 1:
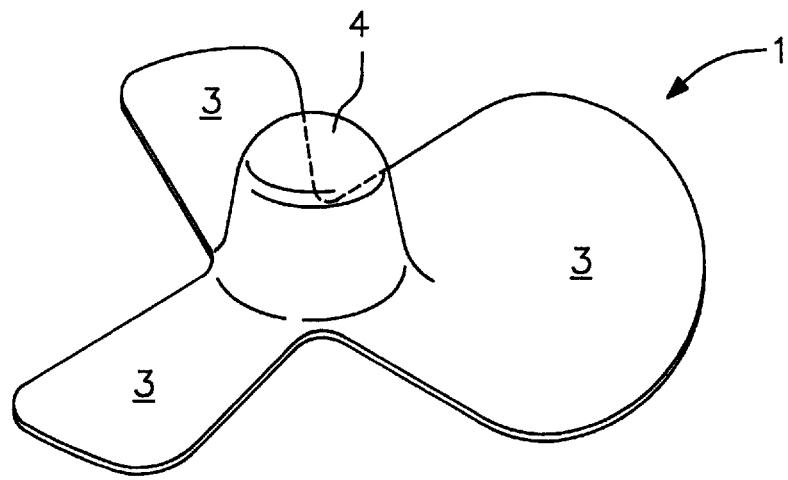
FIG. 1 shows a perspective view of a dressing according to the invention comprising three flaps.

In accordance with the invention it is preferred that the dressing comprises a release liner. A release liner may cover the surface of the adhesive totally or partially. In one embodiment, the release liner only covers the surfaces of flaps constituting second essentially two-dimensional areas leaving the adhesive of the three-dimensional area free, facing a closed space limited by the release liner and the surface of the adhesive. This may be in the form of a dressing as shown in FIG. 1 giving an integral sheet of release liner adhered to the underside of the flaps and closing the concave space of the three-dimensional area.

In the alternative, the dressing of the invention may not comprise a release liner. In this case, the adhesive is protected by the packaging material, e.g. in the form of an individual package comprising one or more dressings.

The second area having an essentially two-dimensional geometry may easily be brought into contact with the skin outside the wound area and enforce the fixation.

A second area may according to the invention be of two-dimensional geometry and may be one or more flaps being integral with the first area or may be constituted by a rim around the first area. The latter embodiment offers the option of an easy adaptation to e.g. a heel or an elbow without increasing the risk of leaking due to large movements outside the area covered by the first area of the dressing of the invention.

It is suitable that the first area of the dressing of the invention has a curvature adapted to a specific part of the body and that the second area of the dressing of the invention is essentially planar. The second area may also be constituted by a single flap being cut in the form of a helix for ensuring an easier adaptation to e.g. a finger as well as a better grip.

The optional application of one or more layers to at least a part of the adhesive of one or both areas to be removed before use ensures that the properties of the adhesive are preserved and that the areas are not laid open until just before the use.

It is preferred to use a carrier film in the form of a thermoplastic polymeric film or a woven or non-woven layer. Such film is preferably also elastic for a better performance in connection with joints being used frequently. The film may be moisture transmitting and may according to the invention be an intelligent film showing a higher moisture vapor permeability when in contact with water than the moisture vapor permeability when not in contact with water. The film may e.g. be made from polymers such as polyolefins e.g. polyethylene, polypropylene or polybutylene, polyamides such as nylons, polyvinyl chloride or polyvinylidene chloride, polyurethanes, ethylene vinyl acetate, styrene-isoprene-styrene block copolymers, ethylene acrylate copolymers, polyesters such as PET, cellulose acetate or other thermoplastic polysaccharides or derivatives thereof.

The carrier film may preferably have a high wearing resistance for use on e.g. knees or elbows.

It is advantageous that the first area of the dressing according to the invention comprises wound healing associated indicator(s), cushions or similar device for treatment or prophylaxis of formation of wounds and/or skin anormalities. This opens for a combined medical treatment of the wound and an easy and sterile application of the active ingredients, e.g. by incorporating active ingredients such as a cytochine such as growth hormone or a polypeptide growth factor giving rise to the incorporation of such active substances in a form being apt to local application in a wound in which the medicament may exercise its effect on the wound, other medicaments such as bacteriostatic or bactericide compounds, e.g iodine, iodopovidone complexes, chloramine, chlorhexidine, silver salts, zinc or salts thereof, metronidazol, sulpha drugs, and penicillins, tissue-healing enhancing agents, e.g. RGD tripeptides and the like, enzymes for cleansing of wounds, e.g. pepsin, trypsin and the like, cytotoxic agents and proliferation inhibitors for use in for example surgical insertion of the product in cancer tissue and/or other therapeutic agents which optionally may be used for topical application, pain releasing agents, emollients, retinoids or agents having a cooling effect which is also considered an aspect of the invention.

In the present context growth hormone is intended to designate any growth hormone which is applicable in accordance with the invention such as human, bovine, ovine, porcine, equine, salmon or tuna growth hormone or analogues or derivatives thereof such as shortened or extended growth hormones such as methionyl growth hormone. A growth hormone is preferably human growth hormone.

Wound healing associated indicator(s) may e.g. be indicators of pH, partial pressure of $O_2$, temperature, radical mechanisms or biotechnological assays, e.g. indicating formation of collagen.

In a preferred embodiment, the first area of the dressing comprises a cushion prepared from a xerogel, preferably an alginate. Such alginate is preferably an alginate not being soluble in water such as calcium alginate.

Such dressings containing a cushion prepared from an alginate are especially suitable for wounds secreting a considerable amount of exudate as such cushions have a considerable capacity for absorbing and keeping liquid. Such a cushion may pre-wetted to form a hydrogel for potentially debriding of ulcer like conditions.

In accordance with the invention, the dressing of the invention may be produced by drawing or moulding, preferably injection moulding, both processes offering the opportunity to tailor both areas of the dressing to obtain a better performance.

In a second aspect, the invention relates to a method for producing a dressing comprising a body facing layer of a thermoplastic adhesive and a carrier film and an absorbent material, said dressing having in itself an outwardly facing convex surface and an inwardly facing concave surface, wherein said dressing comprises a first area facing the wound or skin, said area having essentially three-dimensional geometry and optionally a second area wherein a combined film comprising an adhesive, preferably a hydrocolloid adhesive, a carrier film and optionally a release liner, is inserted into a vacuum mould, the combined film is optionally heated to a temperature typically between 10° C. and 200° C., more normally between 50° C. and 150° C. depending of the actual materials, the combined film is placed between the male part of the mould having a temperature between 10° C. and 200° C., preferably between 40° C. and 110° C., and the female part of the mould having a temperature between 5° C. and 200° C., preferably between 10° C. and 110° C., and a pressure difference of from 0 to 50 at. is established, e.g. a vacuum of up to 0.99 at. is established between the female part of the mould and the combined film, or a superatmospheric pressure of from 0.5 at. to 6 at. is established pressing the film against the female part of the mould using a pressurized medium such as pressurized air (blow-moulding) whereafter the processed laminated film is removed from the mould and cooled, whereafter the rims optionally are trimmed. In the alternative, the film may be pressed directly into the female part of the mould by the action of the male part of the mould without the use of a vacuum or a superatmospheric pressure. When using pressurized air for pressing the film into the female part of the mould, such air is advantageously heated to a temperature of up to 300° C. The pressure, vacuum and temperatures to be applied will vary depending of the specific materials and are easily established by the skilled in the art by routine testing. It is also to be observed that there is a risk of damaging the film if the moulds are heated to high temperatures. When forming the dressings according to the invention by pressing or blow-moulding it is preferred to vent the mould.

Release liner may e.g. be a polyethylene or polyurethane film and is preferably a siliconized polyethylene film or PU film.

Such process is new and offers a very simple process for the manufacture of dressings according to the invention. Furthermore, it was surprisingly found that a combined film comprising a release liner, a hydrocolloid adhesive and a carrier film, e.g. a film of the kind disclosed in U.S. Pat. No. 4,367,732, may be subjected drawing for producing a dressing according to the invention comprising a first area facing the wound or skin, said area having essentially three-dimensional geometry and optionally a second area without deterioration of the properties thereof or delamination.

In one embodiment of the invention the combined film is heated to a temperature of 80° C., the male part of the mould having a temperature of 50° C., and the female part of the mould having a temperature of 20° C. as such temperatures give rise to an easy processing and rapid cooling for allowing rapid de-moulding increasing the production rate but not having adverse effect on the constituents of the dressing or their action.

In a third aspect, the invention relates to a further method for producing a dressing comprising a body facing layer of a thermoplastic adhesive and a carrier film and an absorbent material, said dressing having in itself an outwardly facing convex surface and an inwardly facing concave surface, wherein said dressing comprises a first area facing the wound or skin, said area having essentially three-dimensional geometry and optionally a second area wherein a carrier film and optionally a release film are placed in a mould, e.g. for injection moulding whereafter a thermoplastic adhesive is injected between the films or the carrier film and one part of the mould.

For the same reasons as stated in connection with the process of drawing, it is preferred that the mould is held at a temperature between 10° C. and 160° C., preferably between 20° C. and 110° C., and the thermoplastic adhesive is injected at a temperature between 80° C. and 200° C.

Preferably, the mould is held at a temperature of 20° C. and the thermoplastic adhesive is injected at a temperature of 110° C.

When using injection moulding it is preferred to establish a vacuum between the films and the parts of the mould to separate the films before injecting the thermoplastic adhesive or to separate the films by blowing pressurized air into the mould between the films before injecting the adhesive. Pressurized air is suitably used at a pressure of up to 6 at. and a venting of the parts of the mould is preferably provided for in order to facilitate the forming of the film against the mould.

A release film may according to the invention be placed adjacent to the male part of the mould, the carrier film being placed adjacent to the female part of the mould which gives rise to a dressing having the release liner placed at the inner, concave side of the dressing.

According to the invention it is also foreseen that the carrier film is placed adjacent to the male part of the mould, a release liner being placed adjacent to the female part of the mould which gives rise to a dressing having the release liner placed at the outer, convex side of the dressing.

In a preferred embodiment a process of the invention, a film comprising a cushion layer placed under the release layer adjacent to the adhesive is used as starting material for the drawing process so as to produce a dressing in which the cushion is partly or totally embedded in the adhesive. By this embodiment a cushion layer is placed in the adhesive and will be in direct contact with the wound in use enabling a direct medication.

In accordance with another preferred embodiment a process of the invention, a cushion layer placed in the mould before injecting the adhesive, for preparing a dressing having a cushion layer is placed under the release layer partly or totally embedded in the adhesive.

In a further aspect, the invention relates to the use of a combined film comprising a release layer, a hydrocolloid adhesive and a carrier film for producing a dressing comprising a body facing layer of a thermoplastic adhesive and a carrier film and an absorbent material, said dressing having in itself an outwardly facing convex surface and an inwardly facing concave surface, wherein said dressing comprises a first area facing the wound or skin, said area having essentially three-dimensional geometry and optionally a second area.

In this use, the combined film may e.g. be a film of the kind disclosed in U.S. Pat. No. 4,367,732 comprising several layers or coatings for example a top layer being paper, followed by a siliconized film and a layer of adhesive, a layer of elastic polyurethane, and optionally a thin film of polyethylene, a further layer of paper and finally a coating of silicone wax. The skin barrier may preferably consist of a non-adhesive substantially water-impervious elastic film secured to one of the faces of an adhesive layer of an adhesive material which is a gel-like, at least weakly elastic mixture consisting of a continuous phase consisting of at least one physically cross-linked elastomer selected from the group consisting of styrene-olefin-styrene block copolymers, at least one hydrocarbon tackifier resin selected from the group consisting of polymers and copolymers of cyclopentadiene, dicyclopentadiene, α-pinene, and β-pinene, a polar plasticizer for the elastomer, being compatible with at least with its styrene blocks and decreasing the upper glass transition temperature of the styrene blocks of the elastomer, an antioxidant, and an oily extender, dispersed in the continuous phase a discontinuous phase consisting of at least one hydrocolloid which is swellable in water, the aggregate of said water-impervious elastic film and the adhesive material adhering thereto having low resistance to quick deformation and rapid recovery to substantially the original shape.

In a further aspect, the invention relates to a method of treating a wound on a protruding or retracting part of the body comprising applying a dressing of the invention over the protruding part to contact the surface of the wound thereon.

In this connection "wound" is used to designate not only wounds, but to encompass also psoriasis, eczema, callous skin, corns, blisters, abrasions and the like.

For the purpose of the present invention the expression "film" is used to designate a sheet, layer or laminate without limitation to an essentially two-dimensional tight or impervious material.

The invention is explained more in detail with reference to the drawings.

One embodiment (1) of the invention as shown in FIG. 1 comprises a first area 4 facing the wound or skin, said area having essentially three-dimensional geometry and a second area 3 in the form of three flaps having an essentially two-dimensional geometry. The first area having essentially three-dimensional geometry ensures a good and stable contact to a protruding or retracted part of the body and the second area having an essentially two-dimensional geometry may easily be brought into contact with the skin outside the wound area and enforce the fixation. In accordance with the invention, the adhesive may be placed at the side of the three-dimensional area constituting the internal, concave surface of the dressing when applied to the user in which case the embodiment is especially apt to be used on a finger. The adhesive may, alternatively, be placed at the side of the three-dimensional area constituting the outer, convex surface of the dressing when applied to the user in which case the embodiment is especially apt for rolling the dressing onto e.g. a finger, inverting the dressing, or to be used directly on the interdigital area of a hand or a foot or on deep wounds or cavities. When applying the dressing according to the invention to the interdigital area of a hand or a foot or on deep wounds or cavities, the outwardly facing surface of the dressing in use is concave.

Figure 2:
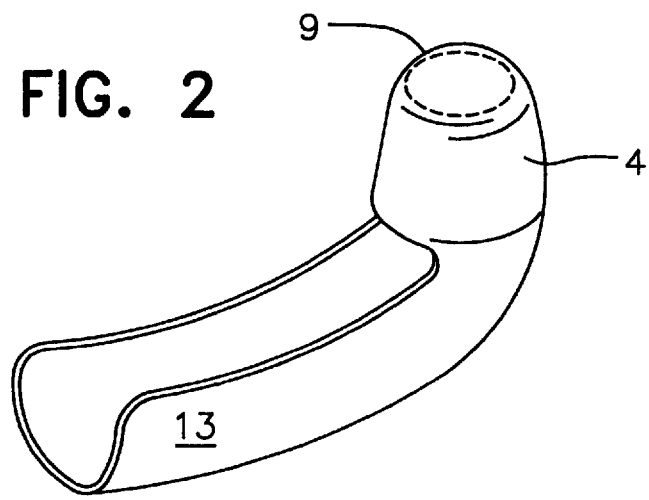
FIG. 2 shows a perspective view of a dressing according to the invention comprising one flap.

FIG. 2 shows another embodiment of a finger dressing according to the invention having a cushion layer 9 partially embedded in the adhesive in the first area 4 having essentially three-dimensional geometry and having a second area having an essentially two-dimensional geometry in the form of one flap 13.

Figure 3:
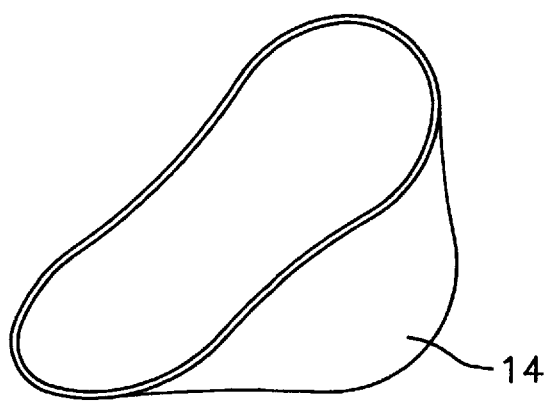
FIG. 3 shows a dressing according to the invention for a heel without tabs.

FIG. 3 shows a further embodiment 14 of the invention especially adapted to cover a heel. In this embodiment, the second area having an essentially two-dimensional geometry may be constituted by a relatively narrow area around the opening of the dressing or may even not be present.

Figure 4:
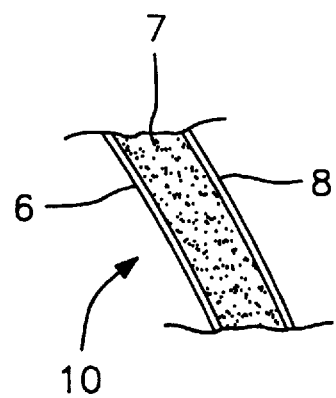
FIG. 4 shows the arrangement of the layers in a dressing according to the invention.

The arrangement of layers 10 in a dressing of the invention shown in FIG. 4 comprises a release liner or film 6, an adhesive layer 7 and a carrier film 8. A further layer or a cushion may be added between the film 6 and the adhesive, e.g. a layer of foam which may serve as a pressure releasing insert. Such pressure releasing insert may be a pressure releasing system known per se, e.g. rings of foam of polystyrene.

The invention is explained more in detail with reference to below working examples which are to be considered illustrative only of principles of the invention and, as all suitable modifications and equivalents may be resorted to, not as limiting the scope of the invention set forth in the appended claims.

MATERIALS AND METHODS

Hydrocolloid adhesive: The recipe of the adhesive is as disclosed in U.S. Pat. No. 4,367,732.

Polyurethane film: Based on Goodrich's Estane® type thermoplastic polyurethanes.

Siliconized polyethylene film: MDPE, 4P-film from Forsheim, Germany

Vacuum moulding apparatus: Formech 450, from Formech Ltd. UK

EXPERIMENTAL PART

Example 1

Preparation of a dressing according to the invention by drawing.

A two-dimensional sheet of a hydrocolloid adhesive consisting of a laminate 10 of a 30 μm thick polyurethane film, a 400 μm thick hydrocolloid adhesive and a 125 μm thick siliconized polyethylene film was moulded into a three-dimensional product by vacuum moulding according to following process. The laminate 10 was heated to 70° C. and thereafter moulded into its final shape by first deforming the material by stretching it from the silicone film side with a positive mould (male part) heated to a temperature of 50° C. followed by a compression into a negative mould (female part) held at a temperature of 30° C. while applying a vacuum of 0.5 bar in the space between the material and the female mould. After setting of the thermoplastic material, the vacuum was set off and the three-dimensional product was de-moulded.

Example 2

Preparation of a dressing according to the invention by drawing

A two-dimensional sheet of hydrocolloid adhesive in the form of a laminate as used in Example 1, but with a 130 μm thick adhesive layer, was heated to 90° C. and moulded with a positive mould heated to a temperature of 70° C. from the side of the siliconized polyethylene film. The positive mould was thereafter combined with the corresponding negative mould held at a temperature of 10° C. under application of a vacuum of 0.5 bar between the blank and the negative mould. After de-moulding, the final three-dimensional product exhibited some anisotrophia due to the relative thin walls in the most stretched zones.

Example 3

Preparation of a dressing according to the invention by drawing

A two-dimensional hydrocolloid adhesive material blank being a laminate (10) consisting of a 35 μm thick LD-polyethylene film, a 350 μm thick hydrocolloid adhesive and a 125 μm thick polyethylene siliconized release film was moulded into a three-dimensional shape in the same manner as described in Example 2.

Example 4

Preparation of a dressing according to the invention by injection moulding

A product with the shape of a heel is produced by injection moulding. A 110 μm polyethylene release film and a 35 μm polyurethane film are fixed between the two parts of the mould. When closing the mould the two films are stretched to the desired shape. Between the two layers of film the molten hydrocolloid adhesive material is injected at a temperature of 110° C. at which temperature the films relaxate due to thermoplastic behaviour.

The three-dimensional product can thereafter be de-moulded from the mould at 50° C.

Example 5

Preparation of a dressing according to the invention by drawing

A dressing was produced in the same manner as described in Example 1, except that it was moulded into a negative shape. By a negative shape is meant a dressing having the siliconized release film on the outer side (the convex side) and the polyurethane film on the inner side (the concave side). The release liner was substituted by a 0.5 mm thick layer of a xerogel-like lyophilised calcium alginate gel in an area of 4 cm² at the tip of the convex side. In a finger dressing this material will have high and fast absorption properties for instant a sorption of blood from e.g. damage of the finger tip.

Example 6

Preparation of a negative or positive shaped dressing as shown in FIG. 1. by drawing After moulding as described in Example 1, the release liner (6) was divided into three parts by application of cuts from the outer rim of the dressing to the tip. The cuts correspond to the flaps (3, 13) in the figures. The number of cuts in the release film liner can, however, be selected after requirement. The dressing in a negative shape is applied to the finger by removal of the siliconized release liner at the top where the cuts meet contacting the finger tip to the open adhesive of the dressing tip and then rolling the dressing onto the finger while gradually removing the silicone liners.

Example 7

Preparation of a dressing according to the invention by drawing

A product for dressing a heel is produced by vacuum moulding in the same manner as described in Example 1 from a two-dimensional sheet laminate consisting of a 25 μm thick plasticized PVC film as carrier film, a 400 μm thick hydrocolloid adhesive and a 110 μm thick siliconized polyethylene release film.

I claim:

1. A dressing comprising a body facing layer of a pressure sensitive adhesive and a carrier film and an absorbent material, said dressing having in itself an outwardly facing convex surface and an inwardly facing concave surface, wherein said dressing comprises a first area facing the wound or skin, said area having essentially three-dimensional geometry and a second area, characterised in that said first area comprises an absorbent thermoplastic hydrocolloid adhesive material and a carrier film, and that said second area is in the form of one or more flaps or a rim having essentially two-dimensional geometry comprising a carrier film and a hydrocolloid adhesive and wherein the adhesive in one or both areas is optionally covered in part or fully by one or more layers to be removed before use.

2. A dressing as claimed in claim 1, wherein the dressing comprises a release liner.

3. A dressing as claimed in claim 1, wherein the carrier film is a thermoplastic polymeric film or a woven or non-woven layer.

4. A dressing as claimed in claim 1, wherein the first area comprises a medication or a cushion for treatment or prophylaxis of formation of wounds and/or skin anomalies and/or wound healing associated indicator.

5. A dressing as claimed in claim 4, wherein the cushion for treatment is a cushion prepared from a xerogel.

6. A method for producing a dressing comprising a body facing layer of a pressure sensitive adhesive and a carrier film and an absorbent material, said dressing having in itself an outwardly facing convex surface and an inwardly facing concave surface, wherein said dressing comprises a first area facing the wound or skin, said area having essentially three-dimensional geometry and a second area in the form of one or more flaps or a rim having essentially two-dimensional geometry comprising a carrier film and a thermoplastic hydrocolloid adhesive, characterised in that a combined film comprising a hydrocolloid adhesive, a carrier film and optionally a release liner, is inserted into a drawing mould, the combined film is heated to a temperature between 10° C. and 200° C., the combined film is placed between the male part of the mould having a temperature between 10° C. and 200° C. and the female part of the mould having a temperature between 10° C. and 200° C. and a pressure difference of from 0 to 50 atmospheres is established pressing or suctioning the combined film against the mould, whereafter the film is removed from the mould and cooled, wherafter the rims optionally are trimmed.

7. A method for producing a dressing comprising a body facing layer of a pressure sensitive adhesive and a carrier film and an absorbent material, said dressing having in itself an outwardly facing convex surface and an inwardly facing concave surface, wherein said dressing comprises a first area facing the wound or skin, said area having essentially three-dimensional geometry and a second area in the form of one or more flaps or a rim having essentially two-dimensional geometry comprising a carrier film and a thermoplastic hydrocolloid adhesive, characterised in that a carrier film and optionally a release film are placed in a corresponding mould, e.g. for injection moulding whereafter a thermoplastic hydrocolloid adhesive is injected between the films.

8. A method as claimed in claim 6, wherein a cushion layer is placed under the carrier layer or release layer so as to be partly or totally embedded in the adhesive.

9. A method of treating a wound on a protruding or retracting part of the body comprising applying a dressing as claimed in claim 1 over the protruding or retracting part to contact the surface of the wound thereon.

10. A dressing as claimed in claim 5, wherein the xerogel is an alginate.

11. A dressing as claimed in claim 10, wherein the alginate is calcium alginate.

12. A method as claimed in claim 7, wherein the mould is an injection mould.

* * * * *